(12) United States Patent
D'Amico

(10) Patent No.: US 10,258,708 B2
(45) Date of Patent: Apr. 16, 2019

(54) CONTROLLED DIFFUSER DEVICE

(71) Applicant: Scent2Market Inc., Yonkers, NY (US)

(72) Inventor: Daniel M. D'Amico, South Salem, NY (US)

(73) Assignee: Scent2Market Inc., Yonkers, NY (US)

( * ) Notice: Subject to any disclaimer, the term of this patent is extended or adjusted under 35 U.S.C. 154(b) by 226 days.

(21) Appl. No.: 14/974,542

(22) Filed: Dec. 18, 2015

(65) Prior Publication Data
US 2016/0271287 A1  Sep. 22, 2016

Related U.S. Application Data

(60) Provisional application No. 62/134,836, filed on Mar. 18, 2015.

(51) Int. Cl.
*A61L 9/00* (2006.01)
*A61L 9/12* (2006.01)

(52) U.S. Cl.
CPC ..................... *A61L 9/12* (2013.01)

(58) Field of Classification Search
CPC ... A61L 9/01; A61L 9/04; A61L 9/015; A61L 9/122; A61L 9/12
USPC ............. 239/35, 55, 59, 57, 60, 50
See application file for complete search history.

(56) References Cited

U.S. PATENT DOCUMENTS 641,548 A * 1/1900 Rose .................. A61L 9/12
239/35
1,380,208 A * 5/1921 Holtschneider .......... A24F 25/02
239/59
1,725,071 A * 8/1929 Gaby ..................... A24F 25/02
239/35

(Continued)

FOREIGN PATENT DOCUMENTS

CN   1333696       1/2002
CN   1333696 A     1/2002

(Continued)

OTHER PUBLICATIONS

International Search Report and Written Opinion for PCT/US2016/02310 dated Aug. 25, 2016.

(Continued)

*Primary Examiner* — Viet Le
(74) *Attorney, Agent, or Firm* — Buchanan Ingersoll & Rooney PC

(57) ABSTRACT

A controlled diffuser device can include a cover, a louver panel, a substrate member, and a base is disclosed. A cover and a base can be configured to affix to each other to sandwich a substrate member and a louver panel while enabling a substrate member and louver panel to slidably engage a base upper surface. A substrate member may comprise a material that changes in a physical dimension as it diffuses aromatic components. Because of static securement and slidable engagement configurations, a louver panel operatively shutters apertures of a cover to selectively moderate varying degrees of exposure of a substrate member as a substrate member changes in a physical dimension. Other embodiments may include a base configured to receive a substrate member and have a cover placed over top. As the substrate changed in physical dimension, the cover can be caused to move relative to the base.

10 Claims, 8 Drawing Sheets

(56) References Cited

U.S. PATENT DOCUMENTS

| | | | | |
|---|---|---|---|---|
| 2,069,179 A | * | 1/1937 | Dunaway | A61L 9/00 206/0.5 |
| 2,438,129 A | * | 3/1948 | Rich | A24F 25/02 222/544 |
| 2,609,230 A | * | 9/1952 | Raleigh | A61L 9/14 239/47 |
| 2,681,827 A | * | 6/1954 | Racz | A24F 19/10 131/231 |
| 2,738,225 A | * | 3/1956 | Meek | A61L 9/12 239/55 |
| 2,765,194 A | * | 10/1956 | Will | A01M 1/2055 239/59 |
| 2,783,084 A | * | 2/1957 | Paxton | A61L 9/12 239/59 |
| 2,794,676 A | * | 6/1957 | D Agostino | F24F 3/16 239/59 |
| 2,942,786 A | * | 6/1960 | Dello Russo | A61L 2/20 221/44 |
| 2,958,469 A | * | 11/1960 | Shuster | A24F 25/02 239/35 |
| 3,104,816 A | * | 9/1963 | Jaffe | A61L 9/12 116/200 |
| 3,239,145 A | * | 3/1966 | Dello Russo | A61L 9/12 206/0.5 |
| 3,804,331 A | * | 4/1974 | Levey | A61L 9/12 239/59 |
| 3,848,803 A | * | 11/1974 | Levey | A01M 1/2055 239/59 |
| D246,110 S | * | 10/1977 | Hadtke | D23/366 |
| 4,128,508 A | | 12/1978 | Munden | |
| 4,155,500 A | * | 5/1979 | Dutcher | B65D 5/18 229/120 |
| 4,219,145 A | * | 8/1980 | Jaeschke | A61L 9/12 229/120 |
| 4,220,281 A | * | 9/1980 | Martens, III | A61B 5/0816 239/57 |
| D258,082 S | * | 1/1981 | Schimanski | 239/59 |
| 4,244,062 A | * | 1/1981 | Corsette | E03D 9/038 239/59 |
| 4,258,874 A | * | 3/1981 | Webinger | A61L 9/12 229/120 |
| 4,270,692 A | * | 6/1981 | Webinger | B65D 5/38 206/0.5 |
| 4,279,373 A | * | 7/1981 | Montealegre | B65D 5/38 206/0.5 |
| 4,280,649 A | * | 7/1981 | Montealegre | A61L 9/12 206/0.5 |
| 4,280,651 A | * | 7/1981 | Montealegre | A61L 9/12 229/122 |
| 4,306,679 A | * | 12/1981 | Dusek | A61L 9/12 239/59 |
| 4,483,095 A | * | 11/1984 | Webinger | A01M 1/02 206/525 |
| 4,523,870 A | * | 6/1985 | Spector | A61L 9/12 239/55 |
| 4,629,330 A | | 12/1986 | Nichols | |
| 4,664,312 A | * | 5/1987 | Bryson | A61L 9/12 206/0.5 |
| 4,795,883 A | | 1/1989 | Glucksman et al. | |
| 4,830,791 A | * | 5/1989 | Muderlak | A61L 9/122 239/35 |
| 4,921,636 A | | 5/1990 | Traas | |
| 5,004,138 A | * | 4/1991 | Gabas | A61L 9/12 224/312 |
| 5,111,477 A | | 5/1992 | Muderlak | |
| 5,163,616 A | * | 11/1992 | Bernarducci | A61L 9/12 239/35 |
| 5,242,111 A | * | 9/1993 | Nakoneczny | A61L 9/127 239/44 |
| 5,269,460 A | | 12/1993 | Hautmann | |
| 5,314,669 A | * | 5/1994 | Hamilton | A61L 9/12 239/52 |
| 5,368,822 A | * | 11/1994 | McNeil | A61L 9/12 239/54 |
| 5,647,052 A | | 7/1997 | Patel et al. | |
| 5,678,763 A | * | 10/1997 | Scheuer | A61L 9/12 239/54 |
| D395,146 S | * | 6/1998 | Miller | D23/355 |
| 5,772,074 A | | 6/1998 | Dial et al. | |
| 6,039,212 A | | 3/2000 | Singh | |
| 6,039,266 A | * | 3/2000 | Santini | A61L 9/048 239/60 |
| 6,227,458 B1 | | 5/2001 | Dever et al. | |
| 6,244,518 B1 | * | 6/2001 | Pogue | A01M 29/12 215/204 |
| 6,340,120 B1 | * | 1/2002 | Seymour | A01M 1/2027 239/34 |
| 6,390,453 B1 | | 5/2002 | Frederickson et al. | |
| 6,471,193 B2 | | 10/2002 | Cole Warren | |
| 6,502,762 B2 | * | 1/2003 | Tuttobene, Jr. | A01M 31/008 222/644 |
| 6,790,670 B2 | | 9/2004 | Munagavalasa et al. | |
| 6,877,674 B2 | * | 4/2005 | Choquet | A61L 9/12 239/34 |
| D504,943 S | * | 5/2005 | Dudley | D15/5 |
| 6,899,281 B1 | | 5/2005 | Griese | |
| D508,285 S | * | 8/2005 | Velicescu | D23/366 |
| D509,578 S | * | 9/2005 | Yao | D23/364 |
| 7,009,519 B2 | | 3/2006 | Leonard et al. | |
| 7,033,990 B2 | | 4/2006 | Dundale et al. | |
| 7,045,000 B2 | * | 5/2006 | Kim | A61L 9/122 239/59 |
| 7,070,172 B2 | * | 7/2006 | Fabrega | A01M 1/2033 239/59 |
| 7,140,553 B2 | * | 11/2006 | Zobele | A61L 9/12 239/34 |
| 7,164,849 B1 | | 1/2007 | Bankers et al. | |
| D544,087 S | * | 6/2007 | Baraky | D23/366 |
| D570,980 S | * | 6/2008 | Isono | D23/366 |
| 7,380,518 B2 | | 6/2008 | Kates | |
| D596,281 S | * | 7/2009 | Schwartz | D23/366 |
| 7,589,340 B2 | | 9/2009 | Danes et al. | |
| D609,322 S | * | 2/2010 | Schwartz | D23/366 |
| 7,670,566 B2 | | 3/2010 | Adair et al. | |
| 7,681,809 B2 | * | 3/2010 | Maget | A01M 1/2044 222/187 |
| D613,845 S | * | 4/2010 | Schwartz | D23/366 |
| D614,278 S | * | 4/2010 | Schwartz | D23/366 |
| 7,845,581 B2 | * | 12/2010 | Wang | A61L 9/042 239/58 |
| 7,883,623 B2 | * | 2/2011 | King | B01F 1/0027 137/268 |
| 8,251,299 B1 | * | 8/2012 | Irvin | A61L 9/12 220/23.83 |
| 8,709,347 B2 | * | 4/2014 | Lackey | A61L 9/12 239/34 |
| 8,740,110 B2 | * | 6/2014 | Gruenbacher | A61L 9/127 220/501 |
| D713,516 S | * | 9/2014 | Belozerova | D23/366 |
| D713,948 S | * | 9/2014 | Westphal | A61L 9/12 D23/366 |
| 8,870,165 B2 | * | 10/2014 | Scolari | A61L 9/122 239/58 |
| 8,882,998 B2 | * | 11/2014 | Tranzeat | A01M 1/2033 210/87 |
| D721,428 S | * | 1/2015 | Donovan | D23/368 |
| D723,150 S | * | 2/2015 | Furner | D23/366 |
| D741,987 S | * | 10/2015 | Gamble | D23/366 |
| D748,772 S | * | 2/2016 | Jacobs | D23/366 |
| D752,198 S | * | 3/2016 | Zach | D23/208 |
| D752,733 S | * | 3/2016 | Zach | D23/208 |
| D780,284 S | * | 2/2017 | Lieberwirth | D22/122 |
| D780,285 S | * | 2/2017 | Lieberwirth | D22/122 |
| 9,591,842 B2 | * | 3/2017 | Furner | A01M 1/02 |
| D806,850 S | * | 1/2018 | D'Amico | D23/366 |
| 2002/0105099 A1 | * | 8/2002 | Warren | A61L 9/12 261/26 |
| 2002/0176704 A1 | * | 11/2002 | Roe | A61L 9/03 392/393 |

(56) References Cited

U.S. PATENT DOCUMENTS

| | | | |
|---|---|---|---|
| 2002/0197188 A1* | 12/2002 | Lua | B01F 3/022 422/124 |
| 2003/0038133 A1* | 2/2003 | Liu | B65D 47/265 220/253 |
| 2003/0089791 A1* | 5/2003 | Chen | A01M 1/2077 239/35 |
| 2003/0152483 A1 | 8/2003 | Munagavalasa et al. | |
| 2003/0188377 A1 | 10/2003 | Contadini et al. | |
| 2004/0045495 A1 | 3/2004 | Yamasaki et al. | |
| 2004/0050950 A1* | 3/2004 | Brown | A01M 1/2055 239/55 |
| 2004/0124988 A1* | 7/2004 | Leonard | B05B 11/0054 340/612 |
| 2004/0188535 A1* | 9/2004 | Hart | A61L 9/048 239/57 |
| 2005/0001053 A1* | 1/2005 | Zobele | A61L 9/12 239/44 |
| 2005/0224595 A1* | 10/2005 | Kuiper | A47L 7/04 239/59 |
| 2006/0100303 A1 | 5/2006 | Bedford et al. | |
| 2007/0290064 A1* | 12/2007 | Majerowski | A01M 1/2044 239/44 |
| 2008/0056691 A1 | 3/2008 | Wingo et al. | |
| 2009/0114736 A1* | 5/2009 | Janakat | A61L 9/127 239/44 |
| 2009/0134239 A1* | 5/2009 | Neumann | A01M 1/2077 239/57 |
| 2009/0302128 A1* | 12/2009 | Zobele | A01M 1/2044 239/59 |
| 2014/0145005 A1* | 5/2014 | Westphal | A61L 9/12 239/59 |
| 2015/0060565 A1 | 3/2015 | Furner | |

FOREIGN PATENT DOCUMENTS

| | | |
|---|---|---|
| CN | 1426313 | 6/2003 |
| CN | 1426313 A | 6/2003 |
| JP | 1379361 | 1/2010 |
| WO | 9215338 | 9/1992 |
| WO | 9215338 A1 | 9/1992 |
| WO | 2004043502 | 5/2004 |
| WO | 2004043502 A1 | 5/2004 |
| WO | 2005003821 | 1/2005 |
| WO | 2005003821 A2 | 1/2005 |

OTHER PUBLICATIONS

First Action of the State Intellectual Property Office of the People's Republic of China dated Jan. 28, 2014.

Supplementary European Search Report for EP Application No. 07852507.8 dated Oct. 13, 2011.

First Office Action of the State Intellectual Property Office of the People's Republic of China for Chinese Application No. 201210341410.3 dated Jan. 28, 2014.

Partial Supplementary European Search Report dated Nov. 6, 2018 for EP 16765819.4.

* cited by examiner

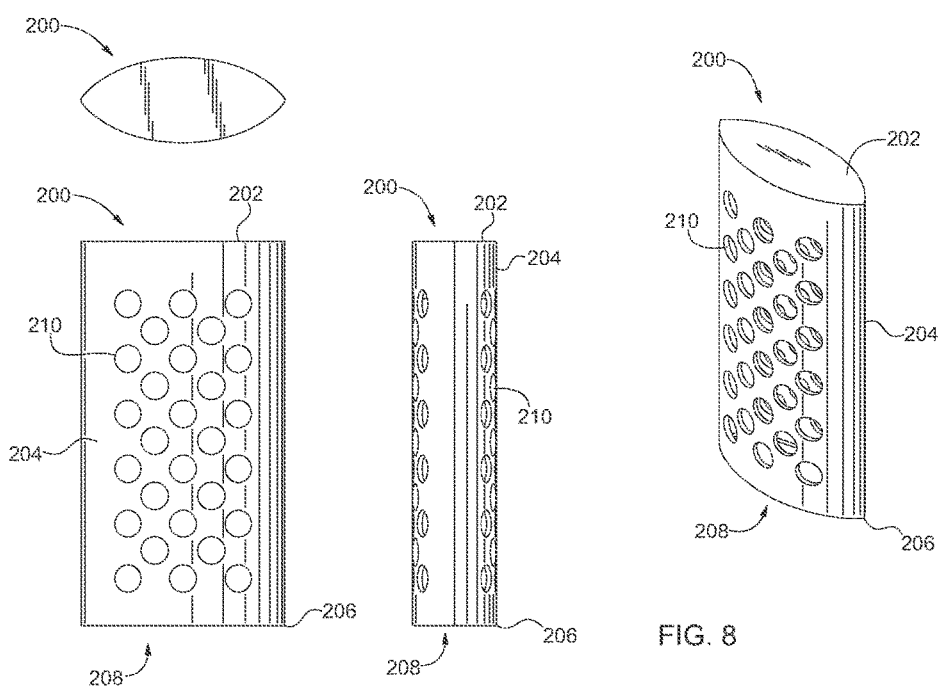

CONTROLLED DIFFUSER DEVICE

CROSS-REFERENCE TO RELATED APPLICATIONS

This patent application claims the benefit of U.S. Provisional Patent Application No. 62/134,836, filed on Mar. 18, 2015, and co-pending U.S. Design patent application Ser. No. 29/541,513 filed Oct. 5, 2015, which are hereby incorporated by reference in their entirety.

FIELD

The present disclosure is generally directed towards a fragrance distribution device; and, in particular, towards a device that controllably diffuses fragrance via an operatively shuttering container.

BACKGROUND

Producing aromatic environments through fragrance-permeation or odor neutralizer-permeation of air occupying a volume of space, such as a room for example, within a vicinity of occupants of that space is well known and a common form of odorizing or de-odorizing that room. Many forms of fragrance-permeation and odor-neutralizer-permeation of air exist.

A common form is the use of a substrate, such as polyethylene vinyl acetate (EVA), laden with fragrance or odor neutralizer components (herein referred to as "aromatic components"). Aromatic components are diffused from the substrate and released into the surrounding air. The aromatic laden substrate is packaged within a container to be substantially in fluid isolation from an environment outside the container. When the container is open or the substrate is removed from the container, a change in vapor pressure initiates the diffusion of the aromatic components.

Typical diffuser containers consist of containers that are either sealed in a closed state to prevent diffusion or open to permit diffusion, whereas the exposure of the substrate is fixed when in a closed state and again fixed when in an open state. Typical diffuser containers do not enable dynamic controllable exposure of the aromatic laden substrate because usually they only enable a fixed amount of exposure when open and a fixed amount of exposure, or non-exposure, when closed. To the extent that additional exposure is required, it must be accomplished manually.

Prior art also fails to provide a means for controllable exposure that is automatic without sophisticated mechanical and/or electrical systems. Typically, as aromatic laden substrates diffuse aromatic components, the chemical potential of diffusion changes over time, especially with an EVA substrate. Consequently, initial diffusion when first exposed occurs at a greater rate, whereas as time lapses and diffusion continues, the diffusion occurs at a lower rate. Prior art, in this regard, further fails to automatically expose the substrate proportionately to the chemical potential of diffusion, which leaves users with an overabundance of fragrance permeation upon initial use and a deficiency of fragrance permeation during later use.

Thus, there is a need for a technical solution to provide a container that automatically and proportionately exposes aromatic laden substrates to maximize effectiveness and efficiency of diffusion by creating an opening in the container commensurate with the level of diffusion desired.

SUMMARY

The present disclosure describes a controlled diffuser device comprising a cover, a louver panel, a substrate member, and a base. A cover may be provided with a cover aperture, and a louver panel may be provided with a tine. A configuration of a disclosed device statically secures a substrate member to a base, statically secures a louver panel to a substrate member, and statically secures a cover to a base. At least one of a substrate member and a louver panel is configured to slidably engage a base upper surface. A cover and a base are configured to affix to each other to sandwich a substrate member to and a louver panel while enabling a substrate member and a louver panel to slidably engage a base upper surface.

A substrate member may comprise a material that changes in physical dimension as it is exposed to a change in vapor pressure and diffuses aromatic components. Because of static securement and slidable engagement configurations described herein, tines of a louver panel operatively shutter apertures of a cover to selectively moderate varying degrees of exposure of a substrate member as a substrate member changes in physical dimension. Therefore a disclosed device provides a means to automatically and proportionately expose aromatic laden substrates to maximize effectiveness and efficiency of diffusion by creating an opening commensurate with a level of diffusion desired.

While these potential advantages are made possible by the technical solutions offered herein, they are not required to be achieved. The presently disclosed device and embodiments thereof can be implemented to achieve technical advantages, whether or not these potential advantages, individually or in combinations, are sought or achieved.

An exemplary embodiment of a controlled diffuser device may comprise the following. At least one cover is provided having a cover upper surface, a cover lower surface, and at least one cover aperture. At least one base is provided having a base upper surface, a base lower surface, and at least one base aperture. At least one louver panel is provided having a louver panel upper surface, a louver panel lower surface, a central member, and at least one tine. At least one louver is provided having a louver upper surface and a louver lower surface, wherein each louver is rotatingly attached to at least one of the at least one cover aperture and the at least one base aperture, wherein the at least one louver is configured to selectively obstruct at least one of the at least one cover aperture and the at least one base aperture.

At least one substrate member is provided having a substrate member first end and a substrate member second end. At least one first end retention mechanism statically secures the at least one substrate member first end to the at least one base upper surface. At least one second end retention mechanism statically secures the louver panel lower surface to the substrate member second end. The at least one louver is in mechanical communication with the substrate member second end. At least one of the at least one substrate member and the at least one louver panel is configured to slidably engage the base upper surface. The substrate member comprises a material that changes at least one physical dimension upon being exposed to a change in vapor pressure.

Upon the change in physical dimension, the substrate member second end is forced to move relative to the substrate member first end, which forces the at least one louver panel in a direction. The at least one substrate member and the at least one louver panel move relative to the at least one base and the at least one cover. As the at least one louver panel moves relative to the at least one cover, the at least one tine traverses an opening of at least one of the at least one cover aperture and the at least one base aperture to regulate exposure of the at least one substrate member to an environment outside of the device.

Upon the change in physical dimension, the substrate member second end is forced to move relative to the substrate member first end, which forces the at least one louver to rotate. The at least one substrate member moves relative to the at least one base and the at least one cover while the at least one louver rotates to selectively obstruct an opening of at least one of the at least one cover aperture and the at least one base aperture to regulate exposure of the at least one substrate member to an environment outside of said device.

Alternative embodiments may provide for the following. The at least one substrate member is provided with aromatic components that diffuse upon the change in vapor pressure. The device further comprises at least one attachment mechanism to affix the device to an ancillary structure. The device further comprises at least one fastening mechanism to affix the at least one cover to the at least one base. The at least one substrate member comprises EVA.

In one embodiment, the device can include a base, a substrate member, and a cover. The base may be a self-supporting container having a bottom with conjoined sides and an open top forming a base interior cavity. The substrate member can exhibit a shape that complements the base interior cavity such that it can be slidingly inserted therein. The cover may have a closed top with conjoined sides and an open bottom forming a cover interior cavity. The cover can be configured such that its cover interior cavity can slidingly receive the base and the substrate member. The base can be structured to stand upright with its open top facing upward. A user can insert the substrate member into the base interior cavity and place the cover over top of the base and substrate member by allowing the cover interior to receive at least the base top and a portion of the substrate member. The cover may be made to rest on top of the substrate member. As the substrate member changes in physical dimension, the cover, due to the fact that it can be resting upon the substrate member, may move relative to the base. At least one of the base sides and cover sides may be provided with at least one vent aperture. As the cover moves relative to the base, the structure of the cover and/or base can shutter or open the vent aperture(s), thus enabling automatic controlled diffusion through the vent aperture(s).

BRIEF DESCRIPTION OF THE DRAWING FIGURES

Exemplary embodiments are best understood from the following detailed description when read in conjunction with the accompanying drawings. Included in the drawings are the following figures:

FIG. 8 is an exemplary second embodiment of a cover.

DETAILED DESCRIPTION

Figure 1:
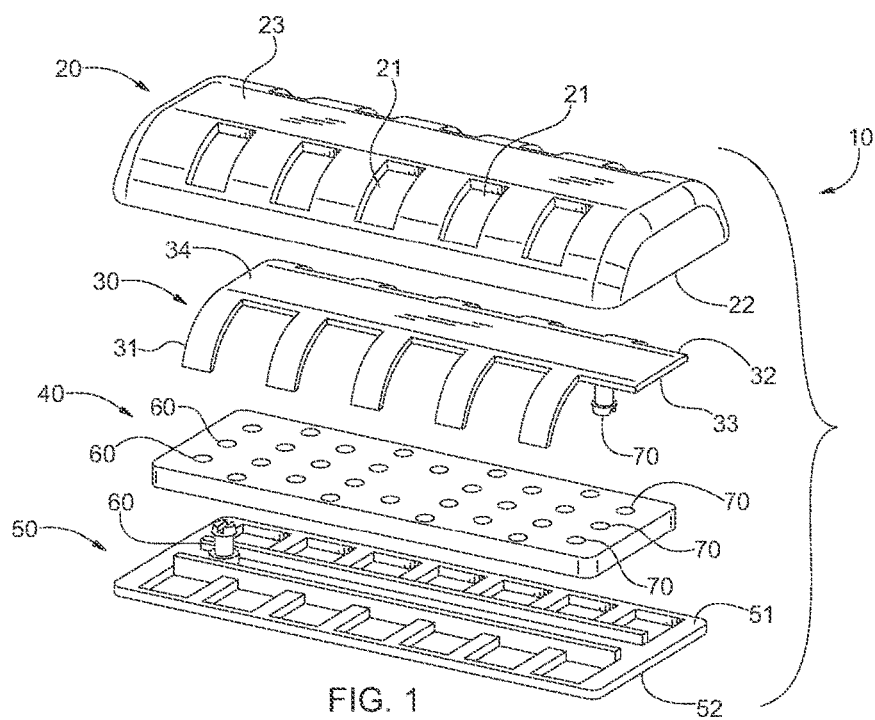
FIG. 1 is an exemplary first embodiment of a device depicting constituent parts in juxtaposition.
Figure 2:
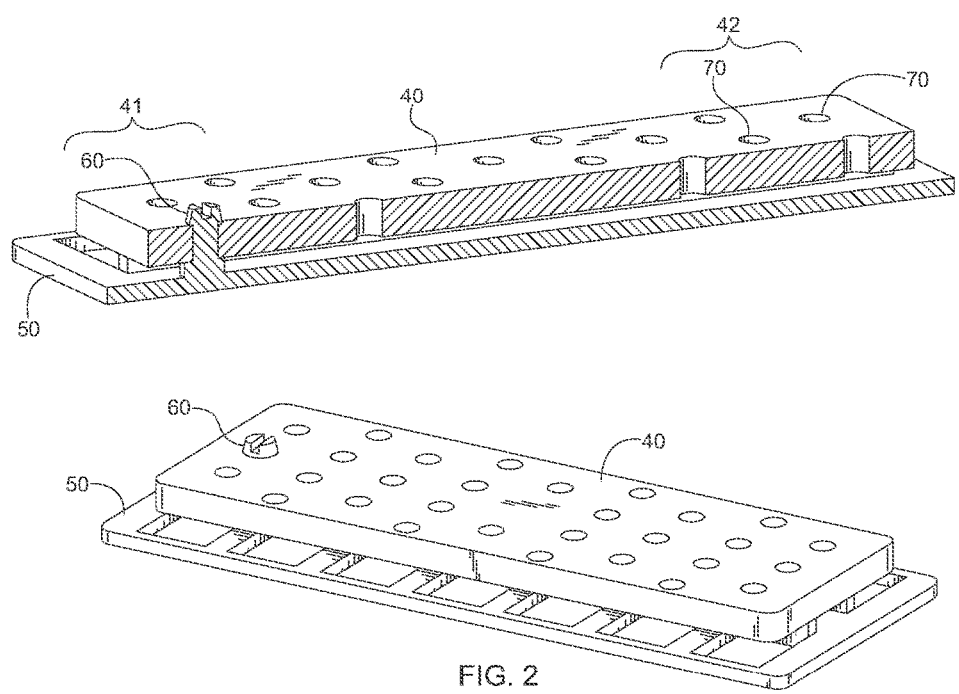
FIG. 2 is an exemplary first embodiment depicting a perspective view of a substrate member secured to a base, and a perspective cross sectional view thereof.
Figure 3:
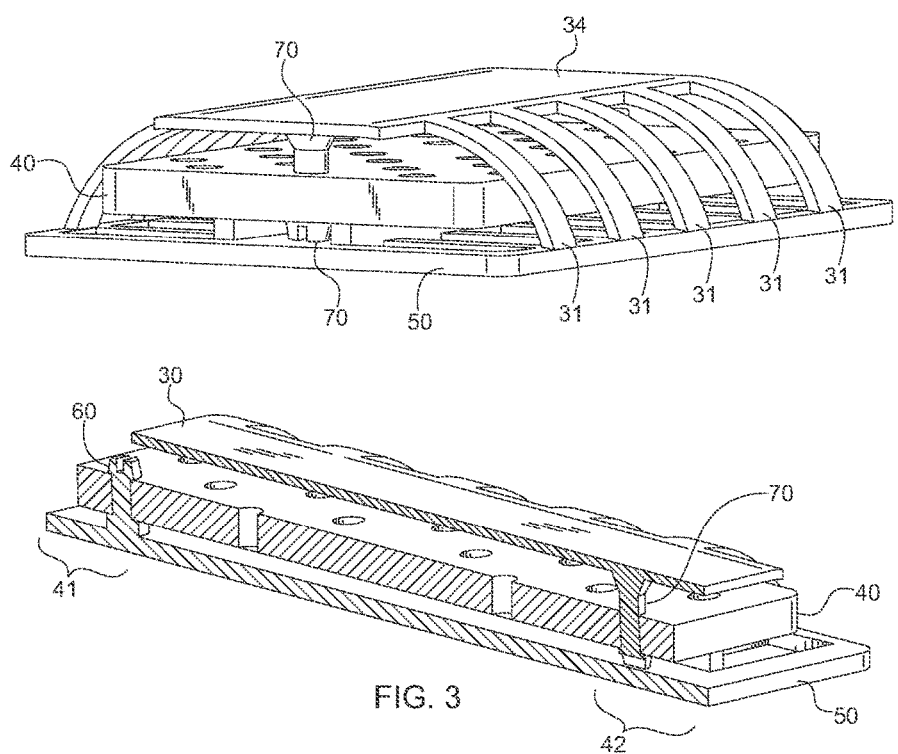
FIG. 3 is an exemplary first embodiment depicting a perspective view of a substrate member secured to a base and a louver panel, and a perspective cross sectional view thereof.

Referring now to FIGS. 1-4, various views of an exemplary first embodiment of a device are disclosed. The present disclosure describes a controlled diffuser device 10 comprising at least one cover 20, at least one louver panel 30, at least one substrate member 40, and at least one base 50. Constituent parts of a cover, a louver panel, and a base may comprise lightweight rigid materials. This may be, for example, plastic, fiberglass, aluminum, steel, ceramic, etc. A cover may be provided with at least one cover aperture 21, and a louver panel may be provided with at least one tine 31. A configuration of a disclosed device statically secures a substrate member first end 41 to a base, statically secures a louver panel 30 to a substrate member second end 42, and statically secures a cover to a base. At least one of a substrate member and a louver is configured to slidably engage a base upper surface 51. A cover and a base are configured to affix to each other to sandwich a substrate member and a louver panel while enabling a substrate member and louver panel to slidably engage a base upper surface.

Figure 4:
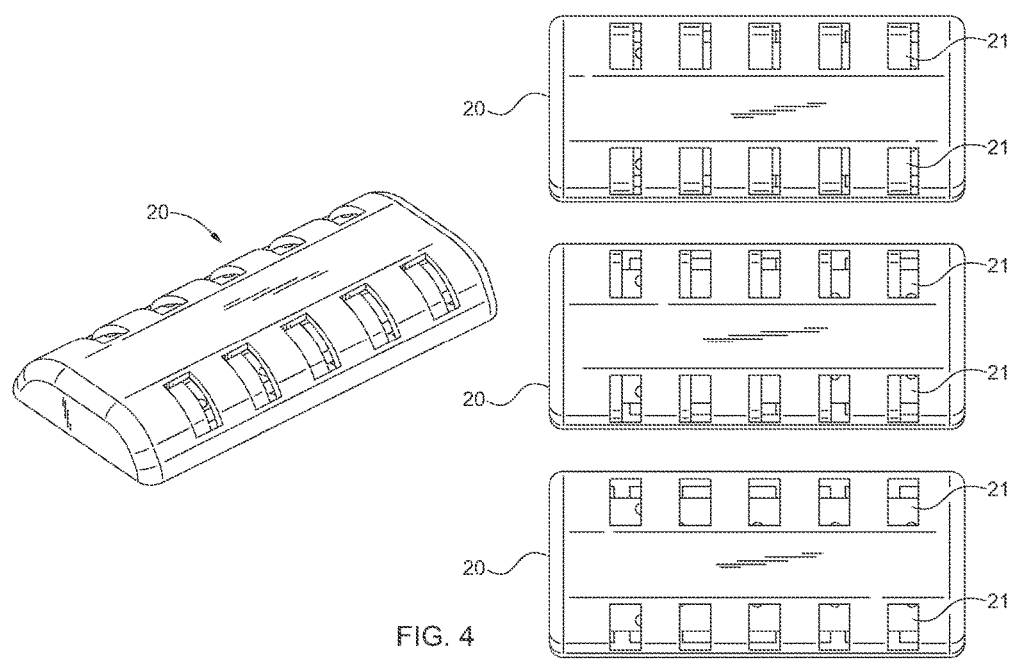
FIG. 4 is an exemplary first embodiment depicting openings of a cover aperture being moderated as a louver panel operatively shutters each opening.
Figure 5:
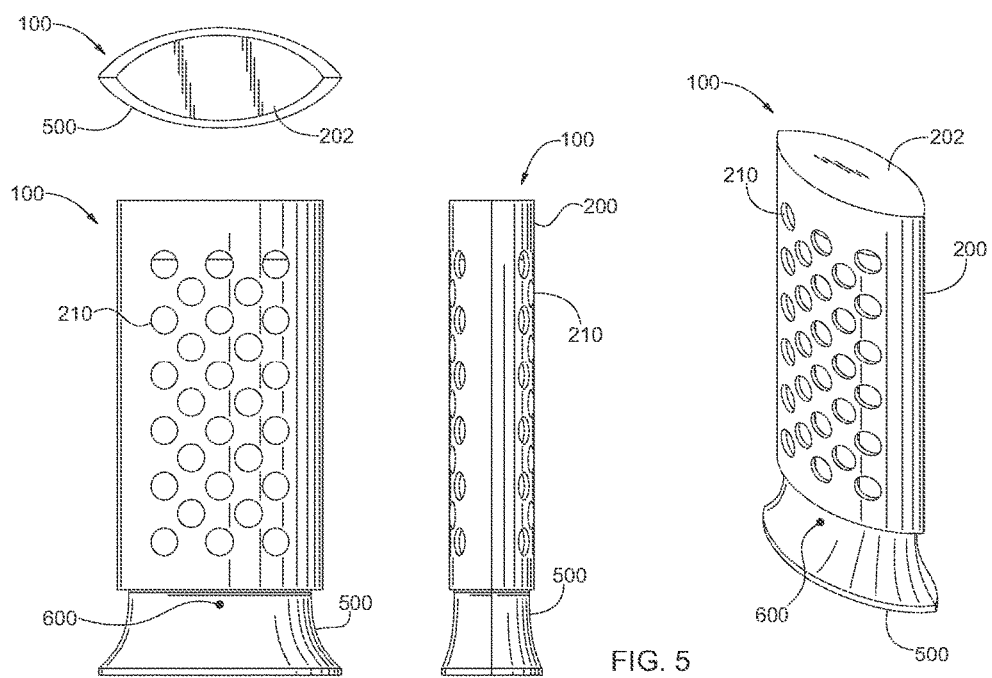
FIG. 5 is an exemplary second embodiment of a device showing a base with a substrate member placed therein and a cover placed over top of a base.

A substrate member may comprise a material that changes in at least one physical dimension as it is exposed to a change in vapor pressure and diffuses aromatic components. In an exemplary embodiment, a substrate member experiences a change in a physical dimension by shrinking. Because of static securement and slidable engagement configurations described herein, as a substrate member changes in a physical dimension a substrate member second end is forced to move relative to a substrate member first end, which forces a louver panel in a direction; a substrate member and a louver panel move relative to a base and a cover; and, as a louver panel moves relative to a cover, a tine traverses an opening of a cover aperture to regulate exposure of a substrate member to an environment outside of a device. Therefore, a louver panel serves as a shutter, selectively moderating varying degrees of exposure of a substrate member as a substrate member changes in a physical dimension, as shown in FIG. 4.

The present disclosure may reference a constituent part in singular, but it is understood that a plurality thereof may be utilized and that any description of singulars is done for the sake of ease of illustration and brevity. It is understood that the same reference may include the singular or plurality of that constituent part without deviating from the teachings of a disclosed device.

While exemplary embodiments of a disclosed device may be illustrated in the figures as having a substantially rectangular shape, it is understood that any ornamental shape facilitating operation of a device consistent with the present disclosure may be utilized.

An exemplary embodiment provides for a base having a base upper surface and a base lower surface 52. A base lower surface may be provided with at least one attachment mechanism to affix a device to an ancillary structure. An ancillary structure may be, for example, a wall, a shelf, a dashboard, etc. An attachment mechanism may be configured to provide for temporary or permanent affixment. An attachment mechanism may be, but is not limited to, a clip, adhesive, hook, or even an eyelet to facilitate a fastener to be inserted therethrough. A portion of a cover may also be provided with a similar attachment mechanism.

A base upper surface may be provided with at least one first end retention mechanism 60 to facilitate securement of a substrate member first end to a base. A substrate member first end may be provided with a complementary first end retention mechanism to enable engagement with a first end retention mechanism of a base upper surface. A retention mechanism may be configured to provide temporary or permanent securement. First end retention mechanisms may comprise at least one retention protrusion extending from a surface of a base upper surface and/or a substrate member first end that is inserted through at least one retention aperture disposed on a surface of a base upper surface and/or substrate member first end. It is understood that other first end retention mechanisms may be utilized. These may be, for example, a clip, adhesive, a spring-loaded pin, etc. First end retention mechanisms may also comprise a rigid member disposed on a substrate member first end and configured to form an interference fit with a portion of a base upper surface.

An exemplary embodiment may provide a louver panel having a louver panel upper surface 32 and a louver panel lower surface 33. A louver panel may comprise a central member 34 with at least one tine extending therefrom. A louver panel lower surface and a substrate member second end may be provided with at least one second end retention mechanism 70, which may be configured as described above for a first end retention mechanism. A second end retention mechanism statically secures a louver panel lower surface to a substrate member second end.

A first end retention mechanism statically secures a substrate member first end to a base upper surface, whereas a second end retention mechanism statically secures a louver panel lower surface to a substrate member second end. A louver panel upper surface may be configured with ornamental features to complement ornamental features of a cover lower surface 22. Such securement configurations and ornamental features enable relative movements of constituent parts for regulated exposure of a substrate member as it changes in a physical dimension.

An exemplary embodiment may provide a cover having a cover upper surface 23 and a cover lower surface 22. A cover may be configured to engage a base via at least one fastening mechanism. Upon engagement with a base, a substrate member and a louver panel are encased by a cover and a base. A fastening mechanism may be configured to removably or permanently affix a cover to a base. A fastening mechanism may be, for example interference fit, clips, adhesive, screw fasteners, etc.

A cover may be provided with at least one cover aperture. A cover lower surface is configured such that at least a portion near at least one cover aperture substantially abuts a least one tine of a louver panel upper surface when a cover is fastened to a base and a substrate member and a louver panel are sandwiched there-between.

In an exemplary embodiment, a device may be assembled such that at least one cover aperture at least partially exposes a substrate member, where a device is then sealed within an ancillary container to be substantially in fluid isolation from an environment outside an ancillary container. As a user removes a device from an ancillary container, diffusion commences because of an initial partial exposure of a substrate member as descried above. As diffusion occurs, a substrate member changes in at least one physical dimension and acts upon a louver panel so that a substrate member second end and a louver panel move relative to a substrate member first end. As a louver panel moves, a tine slides past a cover aperture to create an opening with that aperture, close an opening within that aperture, or modify an opening within that aperture, thereby automatically changing a substrate member's exposure and subjecting a substrate member to a change in vapor pressure. As diffusion occurs, chemical potential to diffuse changes, but a changing vapor pressure creates a change in diffusion rate to counter, reinforce, or otherwise moderate a change in chemical potential to diffuse.

While exemplary embodiments may provide configurations to increase exposure to offset a change in chemical potential, a disclosed device is not limited to such configurations. Configurations may decrease an exposure of a substrate member as it changes in a physical dimension, or alternate between increasing and decreasing exposure as a substrate changes in a physical dimension, or provide various permutations of degrees of exposure as a substrate member changes in a physical dimension. Configurations may change exposure to counter, reinforce, or moderate any change in chemical potential, vapor pressure, or diffusion rate. Configurations may also force relative movements of constituent parts for ornamental or visual effects.

While exemplary embodiments illustrated by the figures depict a single substrate member, it will be envisioned by one skilled in the art with the benefit of this disclosure for there to be a plurality of substrate members and a plurality of louver panels encased by any combination of a single base and a single cover, or a single base and plurality of covers, or a plurality of bases and a single cover.

While exemplary embodiments illustrated by the figures depict a single direction by which directional movement is exploited to operate a louver panel, it is understood that a substrate member may change in physical dimension in any direction, or in all directions, and that any direction may be exploited for this purpose. A substrate member may be configured to change in physical dimension in a direction at a quicker rate than for another direction, or change in physical dimension in overall length in one direction than in another direction. This may be achieved by engineered crystalline structures of the substrate member to exhibit expansion/contraction in preferred directions or to expand/contract in one direction more so than another, providing a substrate member with a dimensional length/width substantially longer than its dimensional width/length, providing a substrate member comprising materials exhibiting different expansions/contractions and aligned in different directions, etc. Furthermore, with a use of multiple constituent parts of a device, multiple directional movements may be exploited simultaneously, in parallel, or in series to operate a louver panel. Therefore, and as by way of example, multiple louver panels may be used with multiple substrate members to provide a complex array of shuttering apertures to regulate exposure of any number of substrate members.

Alternative embodiments may provide for at least one individual louver (not shown), where at least one individual louver may be rotatingly and/or pivotally attached to at least one cover aperture and configured to selectively obstruct a cover aperture. At least one individual louver is in mechanical communication with a substrate member second end so that as a substrate member changes in a physical dimension, a louver rotates and/or pivots to increase or decrease an opening of a cover aperture. Instead of being rotatingly and/or pivotally attached, an individual louver may be slidingly engaged with a cover aperture to operationally shutter a cover aperture (not shown). This may be achieved by having an individual louver slidingly engaged with a track or guide (not shown) of a cover aperture. As a substrate member changes in physical dimension, at least one individual louver is forced to move in a direction and traverse a track or guide. A track or guide may be a structural component disposed on a surface of a cover or base, which supports an individual louver in a suspended position and enables slidable movement of an individual louver. As an individual louver traverses a track or guide, it moderates an opening of an individual cover aperture.

In an alternative embodiment, a base may also be provided with apertures to regulate exposure of a substrate member. In this embodiment, any of the disclosed louver panel embodiments may be used to operatively shutter apertures of such a base in a manner similar as described for operatively shuttering a cover aperture. In this embodiment, a single louver panel may be used to shutter apertures of both a cover and a base. This may be achieved, for example, by providing tines that extend to apertures of a base. Alternately, a louver panel may be utilized for operatively shuttering cover apertures, whereas a separate louver panel may be utilized for operatively shuttering base apertures.

While the figures illustrate a base as a bottom constituent part with a cover as a top constituent part and a substrate member positioned beneath a louver panel, it is understood that a device is not limited to such a serial configuration. One ordinarily skilled in the art would appreciate, with the benefit of the present disclosure, that any combination or permutation of constituent parts and placements thereof may be utilized. As by way of example, in addition to a possible plurality of constituent parts, a device may be configured with a substrate member statically affixed to a cover at its substrate member first end and be slidingly engaged with a cover. As by way of further example a louver panel may be positioned underneath or to a side of a substrate member. As by way of further example, a louver panel may be configured to slidingly engage a cover.

As shown in FIGS. 5-8, in an exemplary second embodiment, the device 100 can include a base 500, a substrate member 400, and a cover 200. The device 100 can be structured so that the base 500 can to stand up-right with the substrate member 400 placed within the base 500. The cover 200 may be placed over top of the base 500 and substrate member 400 and rest upon the substrate member 400. As the substrate member 400 changes in physical dimension, the cover 200 can move relative to the base 500. In some embodiments, the base 500 and/or the cover 200 can include vent apertures 210, which can be shuttered or open as the cover 200 moves relative to the base 500.

The base 500 may be a self-supporting container having a bottom 502 with conjoined sides 504 and an open top 506 forming a base interior cavity 508. The substrate member 400 can be fabricated from the same materials as the substrate member 40 of the first embodiment. The substrate member 400 may exhibit a shape that complements the base interior cavity 508 such that it can be slidingly inserted therein. The cover 200 may have a closed top 202 with conjoined sides 204 and an open bottom 206 forming a cover interior cavity 208. The cover 200 can be configured such that its cover interior cavity 208 can slidingly receive at least the base 506 and the substrate member 400 when the substrate member 400 is inserted into the base interior cavity 508.

Figure 6:
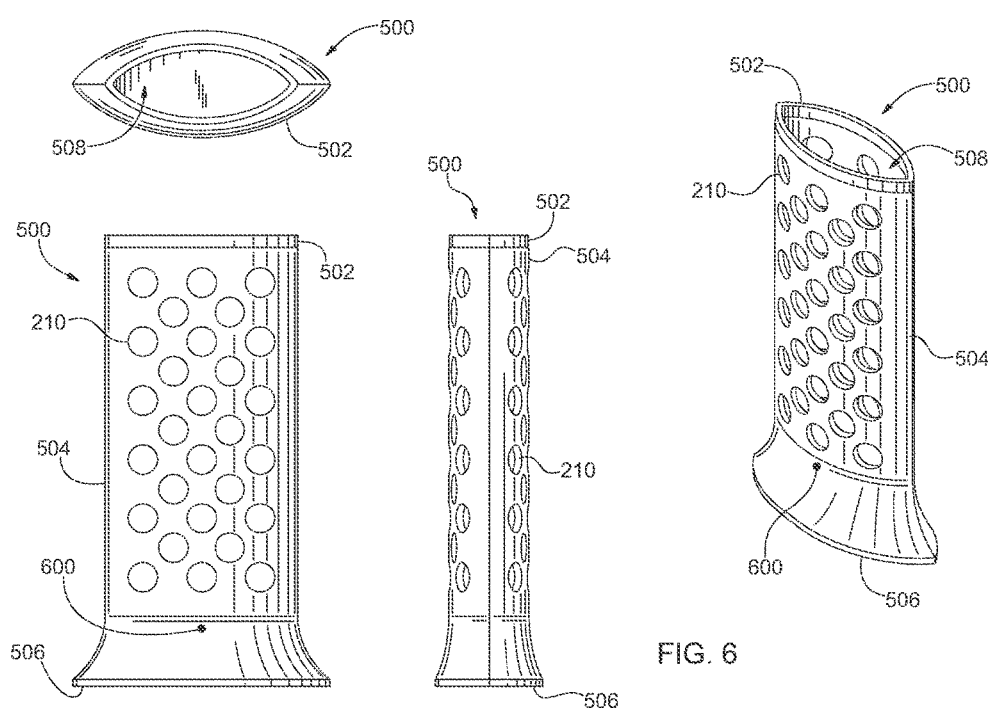
FIG. 6 is an exemplary second embodiment of a base.

Referring to FIG. 6, the base bottom 502 can be structured to facilitate standing the base 500 upright freely with its open top 506 facing upward. For instance, the base bottom 502 can be structured to support the device 100 while resting upon a surface while the base top 506 faces upward from the surface. In addition, the base bottom 502 can exhibit a flare, have support legs, or other similar stand to assist with stability of the base 500 when freely standing upright. The base bottom 502 can be further structured to support the base 500, along with the substrate member 400 when placed inside the base 500 and the cover 200 when placed over top of the base 500, in a free standing upright position. The base 502 is illustrates as being substantially rectangular with rounded edges; however, other shapes can be used. These may include, but are not limited to, cubic, oval, pyramidal, etc. At least one vent aperture 210 can be formed in a side 504 of the base 500. The base interior cavity 508 is shown to have a shape that substantially matches the shape of the base 500; however, the base interior cavity 508 can have a dissimilar shape as that of the exterior of the base 500. For instance, the base 500 exterior can have a pyramidal shape while the base interior cavity 508 may have a rectangular shape.

Figure 7:
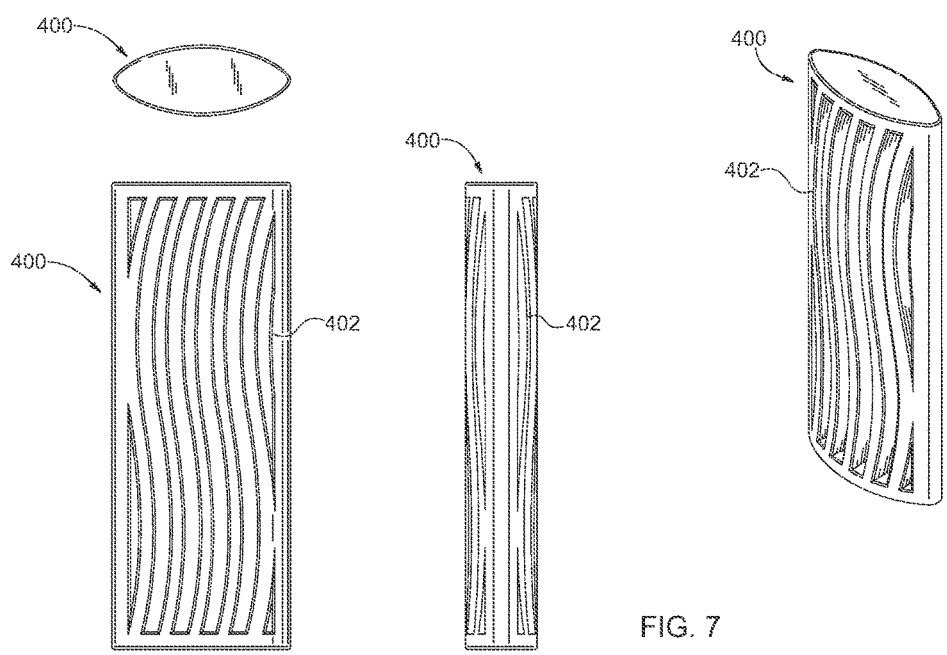
FIG. 7 is an exemplary second embodiment of a substrate member.

Referring to FIG. 7, the substrate member 400 can be structured to slidingly insert into the base interior cavity 508. The substrate member 400 can be shaped to complement the shape of the base interior cavity 508. In some embodiments, the substrate member 400 can have at least one aperture 402 formed within a portion of the substrate member 400. The apertures 402 can extend through a width, length, and/or height of the substrate member 400. Alternatively, or in addition, the apertures 402 can be structured as a dead-hole, recess, and/or depression within a surface of the substrate member 400. The apertures 402 can add ornamentality, but can also increase surface area exposure of the substrate member 400 to increase the rate of diffusion. Furthermore, the apertures 402 can facilitate full dispensement of fragrance from the substrate member 400. For instance, fragrance particles may diffuse from a center of the substrate member 400 and out through an outer surface of the substrate member 400, and if a portion of the substrate member 400 is too thick then it might occur that not all of the fragrance particles diffuse from the substrate member 400 before its useful life. Thus, the apertures 402 can be formed in accordance with the shape of the substrate member 400 and diffusivity to maximize usefulness of the device 100.

The substrate member 400, when laden with fragrance and before it changes in physical dimension due to diffusion of fragrance therefrom, may have a length that is greater than a length defined from the base bottom 502 to the base top 506 (measured from an interior of the base 500). It is contemplated for a portion of the substrate member 400 to protrude from the base interior cavity 508 and extend beyond the base top 506 when the substrate member 400 is placed inside the base interior cavity 508. This may facilitate the cover 200 resting upon the substrate member 400 when the substrate member 400 is placed within the base 500 and the cover 200 is placed over top of the base 500.

Referring to FIG. 8, the cover 200 can be structured to facilitate sliding over and receiving the base 500. The cover 200 can be further structured to facilitate sliding over and receiving the base 500 and the substrate member 400 when the substrate member 400 is placed inside the base 500. The cover 200 is illustrated as being substantially rectangular with rounded edges; however, other shapes can be used. These may include, but are not limited to, cubic, oval, pyramidal, etc. It is contemplated for the cover interior cavity 208 to complement the exterior shape of the base 500, but this is not necessary. The cover interior cavity 208 can be of any shape that enables the cover 200 to be placed over the base 500 and receive the base 500 and/or substrate member 400. At least one vent aperture 210 can be formed in a side 204 of the cover 200. The cover interior cavity 208 is shown to have a shape that substantially matches the shape of the cover 200; however, the cover interior cavity 208 can have a dissimilar shape as that of the exterior of the cover 200. For instance, the cover 200 exterior can have a pyramidal shape while the cover interior cavity 208 may have a rectangular shape.

A user can insert the substrate member 400 into the base interior cavity 508 and place the cover 200 over top of the base 500 and substrate member 400 by allowing the cover interior cavity 208 to receive at least the base top 502 and a portion of the substrate member 400. In embodiments where the substrate member 400 extends beyond the base top 502, the cover 200 may be made to rest on top of the portion of the substrate member 400 extending beyond the base top 502. As the substrate member 400 changes in physical dimension due to diffusion of fragrance therefrom, the cover 200, due to the fact that it can be resting upon the substrate member 400, may move relative to the base 500. For example, the substrate member 400 may shrink in size so that the portion extending beyond the base top 502 advances towards the base bottom 506. This movement may cause the cover 200 to move relative to the base 500. This movement may be the cover 200 moving towards the base bottom 506. At least one of the base side 504 and the cover side 204 may be provided with at least one of the vent apertures 210. As the cover 200 moves relative to the base 500, the structure of the base 500 and/or cover 200 can "shutter" or "open" the vent aperture 210 so as to control diffusion of fragrance from within the device 100. This may be achieved by a vent aperture 210 of the cover 200 traversing a vent aperture 210 and/or structure of the base 500 as the cover 200 is caused to move relative to the base 500.

In some embodiments, the device 10, 100 may include an end-of-life indicator 600. (See FIGS. 5-6). The change in physical dimension of the substrate member 40, 400 can be used as a proxy for useful life of the substrate member 40, 400. For example, it can be predetermined how much of a change in physical dimension of a substrate member 40, 400 would correspond to marginal fragrance diffusion if the substrate member 40, 400 were continued to be used. This change in physical dimension can be designated as the "end-of-useful life" of the substrate member 40, 400. The end-of-useful life physical dimension of the substrate member 40, 400 can be communicated to a user by the configuration of the device 10, 100. Thus, the device 10, 100 can be configured such that when the cover 20, 200 moves relative to the base 50, 500 by an amount that corresponds to the end-of-useful life physical dimension of the substrate member 40, 400, the end-of-life indicator 600 can be made to generate a signal.

The end-of-life indicator 600 may include a marking that provides a signal as to when the useful life of the substrate member 40, 400 has been reached. For example, if an aperture 21, 210, a tine 31, or other structure of the device 10, 100 comes into alignment/misalignment with another aperture 21, 210, tine 31, or other structure of the device 10, 100, then a signal can be generated. The signal can be a colored marking that appears when two apertures 21, 210 align, for example. As another example, the signal can be an illumination source (e.g., light emitting diode) in connection with a circuit that closes and transmits electrical power to the illumination source when two structures align/misalign. As another example, as the cover 200 moves relative to the base 500, an aperture 210 of the cover 200 can come into alignment with a marking made on a base side 504. The marking can be a colored marking or other symbol. The alignment of the aperture 210 with the marking can be used as the end-of-life indicator 600 by structuring the cover 200 and base 500 to not reveal the marking unless the aperture 210 designated as the end-of-life indicating aperture comes into alignment with the marking.

An exemplary embodiment may provide for a substrate member comprising EVA. EVA is a copolymer of ethylene and vinyl acetate. EVA has no odor by its nature; however, it can adsorb or otherwise be permeated with aromatic components. EVA approaches elastomeric materials in softness and flexibility, yet can be processed like thermoplastics. EVA may have a molecular weight in the range of, for example, 10,000 Daltons to 100,000 Daltons, more preferably 22,000 to 87,000 Daltons. Other suitable polymeric materials sharing beneficial properties of EVA may be substituted for use. These may include, but are not limited to, ethyl vinyl alcohol, high density polyethylene, low density polyethylene, polystyrene, acrylic polymers, polycarbonates, polyurethanes, nylons, and mixtures and copolymers of the foregoing.

One or more aromatic components may be used. These may include, but are not limited to, any selected from those compiled by the U.S. Food and Drug Administration in Title 21 of the Code of Federal Regulations, Sections 172.510 and 172.515, incorporated by reference herein. Aromatic components selected from benzaldehydes, phenols, cinnamic aldehydes and esters, octadienes, dienes, cyclohexadienes, and terpenes may be used.

Fragrance oils are also suitable for use alone or in combination with other fragrance chemicals. Suitable fragrance oils are, for example spice oil, flower oil, and fruit oil. Other suitable fragrances include, but are not limited to, benzyl alcohol, ethyl maltol, furaneol, 1-hexanol, cis-3-hexen-1-ol, menthol, benzaldehyde, hexanal, cinnamaldehyde, citral, cis-3-hexenal, furfural, neral, vanillin, ethyl acetate, ethyl butanoate, ethyl decanoate, ethyl hexanoate, ethyl octanoate, hexyl acetate, isoamyl acetate, methyl butanoate, methyl salicylate, pentyl butanoate, pentyl pentanoate, sotolon, strawberry aldehyde, fructone, anethole, anisole, eugenol, dihydrojasmone, 2-acetyl-1-pyrroline, 6-acetyl-2,3,4,5-tetrahydropyridine, gamma-decalactone, gamma-nonalactone, delta-octalactone, jasmine lactone, massoia lactone, camphor, citronellol, linalool, nerol, nerolidol, alpha-terpineol, thujone, and thymol.

Aromatic components may be mixed with one or more hindered amines. Hindered amines are well known in the art and are described in detail in U.S. Pat. No. 6,221,115, the relevant parts of which are incorporated herein by reference. Examples of hindered amines are, but are not limited to: 1-(2-hydroxy-2-methylpropoxy)-4-octadecanoyloxy-2,2,6,6-tetramethylpiperidine; 1-(2-hydroxy-2-methylpropoxy)-4-hydroxy-2,2,6,6-tetramethylpiperidine; bis(1-octyloxy-2,2,6,6-tetramethylpiperidin-4-yl)sebacate; bis(1-cyclohexyloxy-2,2,6,6-tetramethylpiperidin-4-yl)sebacate; 1-cyclohexyloxy-2,2,6,6-tetramethyl-4-octadecylaminopiperidine; 2,4-bis[(1-cyclohexyloxy-2,2,6,6-tetramethylpiperidin-4-yl)butylamino]-6-(2-hydroxyethylamino-s-triazine; bis(1-cyclohexyloxy-2,2,6,6-tetramethylpiperidin-4-yl)adipate; 1-(2-hydroxy-2-methylpropoxy)-4-oxo-2,2,6,6-tetramethylpiperidine; bis(1-(2-hydroxy-2-methylpropoxy)-2,2,6,6-tetramethylpiperidin-4-yl)sebacate; bis(1-(2-hydroxy-2-methylpropoxy)-2,2,6,6-tetramethylpiperidin-4-yl) adipate; bis(1-(2-hydroxy-2-methylpropoxy)-2,2,6,6-tetramethylpiperidin-4-yl)succinate; bis(1-(2-hydroxy-2-methylpropoxy)-2,2,6,6-tetramethylpiperidin-4-yl) glutarate; and 2,4-bis[N-{1-(2-hydroxy-2-methylpropoxy)-2,2,6,6-tetramethylpiperidin-4-yl]-N-butylamino}-6-(2-hydroxyethylamino)-s-triazine) 1-methoxy-4-hydroxy-2,2,6,6-tetramethylpiperidine; 1-methoxy-4-hydroxy-2,2,6,6- tetramethylpiperidine; 1-octyloxy-4-hydroxy-2,2,6,6-tetramethylpiperidine; 1-cyclohexyloxy-4-hydroxy-2,2,6,6-tetramethylpiperidine; 1-methoxy-4-oxo-2,2,6,6-tetramethylpiperidine; 1-octyloxy-4-oxo-2,2,6,6-tetramethylpiperidine; and 1-cyclohexyloxy-4-oxo-2,2,6,6-tetramethylpiperidine, or a mixture thereof.

Aromatic components may include one or more antioxidants. These may include, but are not limited to, tertiary butylhydroquinone, n-octadecyl-3,5-di-tert-butyl-4-hydroxyhydrocinnamate, butylated hydroxyanisole, phenol bisphosphite, butylated hydroxytoluene, and phosphite compounds. An effective amount of antioxidant in the instant composition is 0.015% to 2.5% by weight of the EVA or other polymer, preferably 0.1% to 0.75% by weight and most preferably 0.2% to 0.5% by weight.

Exemplary embodiments may provide for high concentrations of antioxidants mixed with fragrance priori to addition of fragrance/antioxidant mixture to any other components of a mixture.

Inclusion of aromatic components in a diluent may be performed prior to use of a substrate member. Examples of diluents may be, but are not limited to: triethyl citrate; di-isopropyl adipate; di-octyl adipate; isopropyl myristate; isopropyl palmitate; butyl stearate; benzyl alcohol; benzyl benzoate; and diethyl pthalate. Quantities of diluent may be determined by a quantity necessary for dissolving an aromatic components or an antioxidant.

A selected aromatic component (with or without the other additives reported above) may be embedded in and/or adsorbed on a polymer of a substrate member. Aromatic components may be introduced into a polymer at weight percents varying from 10% to 90%, from 20% to 80% from 30% to 70%, from 30% to 60%, and from 30% to 50%. In further embodiments, aromatic components may be introduced into a polymer at a weight percent of about 1%, about 10%, about 20%, about 30%, about 40%, about 50%, about 60%, about 70%, about 80%, about 90%, or about 95%. Further information regarding creation of aromatic components, antioxidants, and diluent mixtures may be found in U.S. Pat. No. 7,220,288, which is incorporated by reference as if fully rewritten herein.

Further areas of applicability of the present disclosure will become apparent from the detailed description provided hereinafter. It should be understood that the detailed description of exemplary embodiments are intended for illustration purposes only and are, therefore, not intended to necessarily limit the scope of the disclosure.

While various exemplary embodiments of the disclosed device have been described above it should be understood that they have been presented for purposes of example only, not limitations. It is not exhaustive and does not limit the disclosure to the precise form disclosed. Modifications and variations are possible in light of the above teachings or may be acquired from practicing of the disclosure, without departing from the breadth or scope.

What is claimed is:

1. A shuttering device, comprising:
    a base having a base bottom with conjoined base sides and an open base top forming a base interior cavity;
    a substrate member comprising fragrance, said substrate member configured to slidbaly insert into said base interior cavity, wherein said substrate member further comprises a material that changes at least one physical dimension upon being exposed to a change in conditions; and,
    a cover having a cover top with conjoined cover sides and an open cover bottom forming a cover interior cavity, said cover interior cavity configured to receive at least said base top and a portion of said substrate member when said substrate member is inserted into said base interior cavity and said cover is placed over top of said base;
    wherein:
        said substrate member is configured to sit within said base interior cavity such that when said cover is placed over top said base, said cover rests upon said substrate member;
        when said substrate member changes at least one physical dimension, said cover moves relative to said base;
        said base side has at least one base vent aperture and said cover has at least one cover vent aperture;
        said at least one base vent aperture and said at least one cover vent aperture are shuttered and/or opened as said cover moves relative to said base; and
        said shuttering and/or said opening of said at least one base vent aperture and said at least one cover vent aperture increases a diffusion rate of the fragrance from said substrate member by increasing exposure of said substrate member as said substrate member changes in the at least one physical dimension.

2. The device recited in claim 1, wherein said substrate member has at least one aperture formed therein.

3. The device recited in claim 1, further comprising an end-of-life indicator.

4. The device recited in claim 3, wherein said end-of-life indicator comprises a signal generator that generates a signal when said at least one vent aperture of said base side and said at least one vent aperture of said cover are aligned.

5. The device recited in claim 1, wherein said base bottom is structured to cause the base to stand freely upright with said base top facing upwards.

6. The device recited in claim 1, wherein said base bottom is structured to cause the base to stand freely upright with said base top facing upwards with said substrate member inserted into said base and said cover placed over top of said base.

7. The device recited in claim 1, wherein said cover top is closed.

8. The device recited in claim 1, wherein said base bottom has a flare to assist with stability of the device.

9. The device recited in claim 1, wherein said base is configured to allow at least a portion of said substrate to extend beyond said open base top.

10. The device recited in claim 1, wherein the movement of said cover relative to said base comprises said cover moving towards said base.

* * * * *